United States Patent
Ando et al.

(10) Patent No.: US 6,207,172 B1
(45) Date of Patent: *Mar. 27, 2001

(54) COMPOSITION FOR THE DELIVERY OF A PHARMACEUTICAL AGENT TO A PATIENT

(75) Inventors: Howard Yoshihisa Ando, Ypsilanti; Steven Edward Rose, Ann Arbor, both of MI (US)

(73) Assignee: Warner-Lambert Company, Morris Plains, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/177,140

(22) Filed: Oct. 21, 1998

Related U.S. Application Data

(60) Provisional application No. 60/064,285, filed on Oct. 30, 1997.

(51) Int. Cl.$^7$ ............................. A61K 9/00; A61K 31/505
(52) U.S. Cl. ........................ 424/400; 424/427; 424/430; 424/434; 424/435; 424/436; 424/486; 514/256
(58) Field of Search ............................................. 424/486

(56) References Cited

U.S. PATENT DOCUMENTS 5,599,808 * 2/1997 Goldstein ............................. 514/211
5,897,858 * 4/1999 Haslwanter ........................ 424/78.04

* cited by examiner

Primary Examiner—Gollamudi S. Kishore
(74) Attorney, Agent, or Firm—Todd M. Crissey; Michael J. Atkins; Charles W. Ashbrook

(57) ABSTRACT

The present invention relates to a composition for the delivery of a pharmaceutical agent to a patient that comprises polyethylene glycol, an aqueous solution containing polyvinylpyrrolidone, and a pharmaceutical agent. The invention also relates to methods of making a composition for the delivery of a pharmaceutical agent.

12 Claims, No Drawings

COMPOSITION FOR THE DELIVERY OF A PHARMACEUTICAL AGENT TO A PATIENT

CROSS-REFERENCE TO RELATED APPLICATION

This application claims priority of U.S. Ser. No. 60/064,285, filed Oct. 30, 1997.

FIELD OF THE INVENTION

The present invention relates to a composition for the delivery of a pharmaceutical agent to a patient. The invention also relates to methods of making a composition for the delivery of a pharmaceutical agent.

BACKGROUND OF THE INVENTION

The delivery of pharmaceutical agents to patients can be difficult when the pharmaceutical agent to be delivered is highly lipophilic and/or poorly water soluble. For example, one common method of delivering or administering a pharmaceutical agent is by subcutaneous injection. In order to subcutaneously inject a pharmaceutical agent into a patient, the pharmaceutical agent is typically dissolved in or mixed with a solvent, most preferably water. If the pharmaceutical agent can not be dissolved in or mixed with an acceptable solvent such as water, it cannot be administered subcutaneously. Similar problems are seen when a pharmaceutical agent is to be administered to a patient orally in a solution. Because many pharmaceutical compounds are highly lipophilic and/or poorly water soluble, there is a need for compositions that can be used to deliver these pharmaceutical agents.

SUMMARY OF THE INVENTION

The present invention provides a composition for the delivery of a pharmaceutical agent to a patient, the composition comprising polyethylene glycol having a weight-average molecular weight in the range of about 1,300 to about 9,000, an aqueous solution containing from about 5% (w/v) to about 20% (w/v) polyvinylpyrrolidone with respect to the entire solution, the polyvinylpyrrolidone having a weight-average molecular weight in the range of about 2,000 to about 30,000, and a pharmaceutical agent.

In one embodiment of the invention, the polyethylene glycol has a weight-average molecular weight in the range of about 1,300 to about 4,800.

In a preferred embodiment of the invention, the polyethylene glycol has a weight-average molecular weight in the range of about 3,000 to about 4,800.

In another preferred embodiment of the invention, the polyvinylpyrrolidone is about 20% (w/v) of the aqueous solution.

In another preferred embodiment of the invention, the polyvinylpyrrolidone has a weight-average molecular weight of about 10,000.

In one embodiment of the invention, the pharmaceutical agent is highly lipophilic or poorly water soluble.

In another embodiment of the invention, the aqueous solution is water.

In still another embodiment of the invention, the aqueous solution is a biologically compatible buffer having a pH in the range of about 1.0 to about 7.4.

In a more preferred embodiment of the invention, the biologically compatible buffer is a phosphate buffer.

In another preferred embodiment of the invention, the polyethylene glycol is present in the composition in an amount that is in the range of about 20% to about 70% by volume of the composition.

In a more preferred embodiment of the invention, the polyethylene glycol is present in the composition in an amount that is in the range of about 40% to about 60% by volume of the composition.

In a most preferred embodiment of the invention, the polyethylene glycol is present in the composition in an amount that is about 50% by volume of the composition.

In a preferred embodiment, the aqueous solution is present in the composition in an amount that is in the range of about 20% to about 70% by volume of the composition.

In a more preferred embodiment, the aqueous solution is present in the composition in an amount that is in the range of about 40% to about 60% by volume of the composition.

In a most preferred embodiment, the aqueous solution is present in the composition in an amount that is about 50% by volume of the composition.

Also provided is a method of making a pharmaceutical composition, the method comprising melting solid polyethylene glycol having a weight-average molecular weight in the range of about 1,300 to about 9,000, adding a pharmaceutical agent to the molten polyethylene glycol to form a polyethylene glycol/pharmaceutical agent combination, and combining the polyethylene glycol/pharmaceutical agent combination with an aqueous solution of polyvinylpyrrolidone, the polyvinylpyrrolidone having a weight-average molecular weight in the range of about 2,000 to about 30,000.

Also provided is a method of making a pharmaceutical composition, the method comprising combining a pharmaceutical agent with solid polyethylene glycol having a weight average molecular weight in the range of about 1,300 to about 9,000 to form a polyethylene glycol/pharmaceutical agent combination, and combining the polyethylene glycol/pharmaceutical agent combination with an aqueous solution of polyvinylpyrrolidone, the polyvinylpyrrolidone having a weight-average molecular weight in the range of about 2,000 to about 30,000.

In a preferred embodiment of the methods of making a pharmaceutical composition, the polyethylene glycol has a weight-average molecular weight in the range of about 1,300 to about 4,800.

In a more preferred embodiment of the methods of making a pharmaceutical composition, the polyethylene glycol has a weight-average molecular weight in the range of about 3,000 to about 4,800.

In a preferred embodiment of the methods of making a pharmaceutical composition, the polyvinylpyrrolidone is about 20% (w/v) of the aqueous solution.

In a preferred embodiment of the methods of making a pharmaceutical composition, the polyvinylpyrrolidone has a weight-average molecular weight of about 10,000.

In a preferred embodiment of the methods of making a pharmaceutical composition, the pharmaceutical agent is highly lipophilic or poorly water soluble.

In a preferred embodiment of the methods of making a pharmaceutical composition, the aqueous solution is water.

In a preferred embodiment of the methods of making a pharmaceutical composition, the aqueous solution is a biologically compatible buffer having a pH in the range of about 1.0 to about 7.4.

In a preferred embodiment of the methods of making a pharmaceutical composition the buffer is a phosphate buffer.

In a preferred embodiment of the methods of making a pharmaceutical composition the polyethylene glycol is present in the composition in an amount that is in the range of about 20% to about 70% by volume of the composition.

In a preferred embodiment of the methods of making a pharmaceutical composition the polyethylene glycol is present in the composition in an amount that is in the range of about 40% to about 60% by volume of the composition.

In a most preferred embodiment of the methods of making a pharmaceutical composition, the polyethylene glycol is present in the composition in an amount that is about 50% by volume of the composition.

In a preferred embodiment of the methods of making a pharmaceutical composition, the aqueous solution is present in the composition in an amount that is in the range of about 20% to about 70% by volume of the composition.

In a preferred embodiment of the methods of making a pharmaceutical composition, the aqueous solution is present in the composition in an amount that is in the range of about 40% to about 60% by volume of the composition.

In a preferred embodiment of the present invention, the aqueous solution is present in the composition in an amount that is about 50% by volume of the composition.

In a preferred embodiment of the methods, the composition is autoclaved, freeze dried, or extruded.

DETAILED DESCRIPTION OF THE INVENTION

The present invention relates to a composition that can be used to deliver a pharmaceutical agent to a patient. The term "patient" means all animals including humans. Examples of patients include humans, cows, dogs, cats, goats, sheep, and pigs.

A pharmaceutical agent is a chemical compound that when administered to a patient has a biological effect on the patient. Examples of pharmaceutical agents include, but are not limited to, compounds given to a patient to treat cancer, AIDS, inflammation, diabetes, high blood pressure, atherosclerosis, Altzheimer's disease, bacterial or viral infection, high cholesterol, depression, obesity, emesis, dementia, stroke, restenosis, and cerebral ischemia. The pharmaceutical agents of the present invention are typically highly lipophilic and/or poorly water soluble. A highly lipophilic compound is a compound that has a log P (octanol/water) value greater than about 2. Similarly, a poorly water soluble compound is a compound that has a solubility in water at 25° C. of less than about 1 mg/mL. The pharmaceutical agents of the present invention can be solids or liquids.

The composition of the present invention comprises a mixture of polyethylene glycol, an aqueous solution containing polyvinylpyrrolidone, and a pharmaceutical agent.

The polyethylene glycol polymer is typically solid and has a weight-average molecular weight in the range of about 1,300 to about 9,000. In a preferred embodiment, the molecular weight of the polyethylene glycol is in the range of about 1,300 to about 4,800, and more preferably in the range of about 3,000 to about 4,800. A most preferred molecular weight of the polyethylene glycol is in the range about 3,000 to about 3,700.

The aqueous solution comprises either water or a buffer and polyvinylpyrrolidone. The buffer can be any buffer that is known to those skilled in the art that is suitable for administration to a patient, particularly humans. The pH of the buffer is preferably in the range of about 1.0 to about 7.4. A preferred buffer is a phosphate buffer.

The aqueous solution is present in the composition for the delivery of a pharmaceutical agent in the range of about 20% to about 70% by volume of the composition. Preferably, the aqueous solution is present in the composition in the range of about 40% to about 60% by volume of the composition. More preferably, the aqueous solution is present in the composition at about 50%.

The polyvinylpyrrolidone component of the aqueous solution comprises polyvinylpyrrolidone that has a weight-average molecular weight in the range of about 2,000 to about 30,000. Preferably, the molecular weight of the polyvinylpyrrolidone is about 10,000.

The polyvinylpyrrolidone is about 5% to about 20% (w/v) of the aqueous solution. Preferably, the polyvinylpyrrolidone is about 20% (w/v) of the aqueous solution.

The polyethylene glycol is present in the composition for the delivery of a pharmaceutical agent in the range of about 20% to about 70% by volume of the composition. Preferably, the polyethylene glycol is present in the composition in the range of about 40% to about 60%. Most preferably, the polyethylene glycol is present in the composition at about 50%. When using polyethylene glycol having a molecular weight in the range of about 7,000 to about 9,000, the amount of polyethylene glycol present in the composition is about 10% to about 20% by volume of the composition due to high viscosities of the composition when the amount of polyethylene glycol is over about 20%.

The composition of the present invention can be made by first melting the solid polyethylene glycol and then adding the pharmaceutical agent to the molten polyethylene glycol to form a polyethylene glycol/pharmaceutical agent combination. Then, the polyethylene glycol/pharmaceutical agent combination can be combined with the aqueous solution to form the composition. Alternatively, the polyethylene glycol/pharmaceutical agent combination can be cooled after the addition of the pharmaceutical agent until it solidified, solidification can occur and the solidified polyethylene glycol/pharmaceutical agent combination can be combined with the aqueous solution. Moreover, the polyethylene glycol, pharmaceutical agent and aqueous solution containing polyvinylpyrrolidone can be simply mixed together.

While not wishing to be bound by theory, the resulting composition for delivery of a pharmaceutical agent is thought to form a composition in which the pharmaceutical agent is dispersed within or microencapsulated by the polyethylene glycol to form a droplet or sphere, which is dispersed as an emulsion within the polyvinylpyrrolidone containing aqueous solution. Using laser confocal scanning microscopy and a pharmaceutical agent that has fluorescent properties, it was discovered that the pharmaceutical agent was uniformly dispersed through out the interior of each droplet. The use of laser confocal scanning microscopy allows the viewing of slices as small as 1 mm through the encapsulating sphere.

Polyvinylpyrrolidone concentrations of 0, 1, 2.5, 5, 10, and 20% (w/v) with respect to the composition were used prepared, and it was determined that a minimum of about 5% was required.

In addition, various polymers were used instead of polyethylene glycol. Also, various mixtures of different molecular weights of polyethylene glycol were investigated. The following polymers and polymer mixtures were tested:

Pluronic F 127 Prill (BASF, Parsippany, N.J.);
Pluronic F 108 Prill (BASF, Parsippany, N.J.);
polyoxyl 40 stearate;

sorbitan monostearate;
Sterotex;
stearic acid;
cetyl alcohol;
glycerol monostearate;
PEG 400 (Sigma, St. Louis, Mo.);
PEG 600 (Sigma, St. Louis, Mo.);
PEG 1000 (Sigma, St. Louis, Mo.);
1:1:1 PEG 1000:PEG 3350: PEG 8000;
1:1 PEG 400: PEG 8000; and
1:1 PEG 1450: PEG 3350.
None of the above polyethylene glycol substitutes were successful.

In addition, the following compounds were tried in place of polyvinylpyrrolidone:
Avicel PH 101;
hydroxypropyl cellulose;
corn starch; and
hydroxymethyl cellulose.
None of the above polyvinylpyrrolidone substitutes were successful.

After formation of the composition for delivering a pharmaceutical agent to a patient, the composition has been successfully extruded through both 0.45 and 0.2 mm nylon filters, yielding a particle size of around 500 or 300 nm, respectively. In addition, the compositions can be autoclaved. The compositions have also been freeze dried and can be reconstituted by the addition of water or a buffer.

The compositions can be administered to humans and animals either orally, rectally, parenterally (intravenously, intramuscularly or subcutaneously), intracisternally, intravaginally, intraperitoneally, intravesically, locally (ointments or drops), or as a buccal or nasal spray.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Liquid dosage forms for oral administration include pharmaceutically acceptable emulsions, solutions, suspensions, syrups and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

The examples presented below are intended to illustrate particular embodiments of the invention and are not intended to limit the scope of the specification, including the claims, in any manner.

EXAMPLES

The compositions of the present invention were made by the following methods.

Method I
1. Weigh a mass of polyethylene glycol which, when adjusted for density, will occupy a volume of one-half the total volume of the final composition.
2. Heat the polyethylene glycol to melting (e.g., 55 to 60° C. for PEG 3350, Sigma, St. Louis, Mo.).
3. Dissolve bulk pharmaceutical agent into the molten PEG.
4. With stirring, add about an equal volume of 20% (w/v) PVP solution made either in water or a buffer.
5. Allow the resulting combination to cool to room temperature.

Method II
1. Weight a mass of polyethylene glycol which, when adjusted for density, will occupy a volume of one-half the total volume of the final composition.
2. Add bulk pharmaceutical agent to the solid PEG.
3. With stirring, add about an equal volume of 20% (w/v) PVP solution made either in water or a buffer.

In Vivo Tests
Pharmaceutical compositions were made as described above using various pharmaceutical agents. The pharmaceutical composition were administered to mice.

Example 1

Formulation
$N^4$-(3-Bromo-phenyl)-$N^6$-methyl-pyrido[3,4-d]pyrimidine-4,6-diamine (irreversible tyrosine kinase inhibitor) was formulated in the PEG/PVP system as follows. Sixty milligrams of $N^4$-(3-bromo-phenyl)-$N^6$-methyl-pyrido[3,4-d]pyrimidine-4,6-diamine were dissolved in 3 g of molten (65° C.) PEG 3350. To the melted phase were then added 3 mL of 10% PVP in pH 7.4 phosphate buffer with stirring. The mixture was stirred during cool-down to room temperature. Before administration, the formulation was filtered through a 0.45 μm PTFE filter. Mean particle size was shown to be approximately 400 nm diameter. The final concentration was calculated to be 10 mg/mL.

Administration and Study Design
Single, 200-mg/kg daily oral gavage doses of the PEG/PVP formulation were given to 3 tumor-bearing mice for 10 days. In parallel, a 400-mg/kg (200 mg/kg oral gavage, twice daily) dose of $N^4$-(3-bromo-phenyl)-$N^6$-methyl-pyrido[3,4-d]pyrimidine-4,6-diamine was administered to 3 additional tumor-bearing mice in a formulation consisting of 10 mg/mL drug in DMA/lactate (prepared by Cancer Therapeutics group) for 10 days. After 10 days, $N^4$-(3-bromo-phenyl)-$N^6$-methyl-pyrido[3,4-d]pyrimidine-4,6-diamine blood levels were measured by HPLC assay, and change in tumor size from Day 1 was determined for both dose groups (compared to a control, untreated group of tumor-bearing mice).

Results

Tumor growth inhibition was 4-fold greater in mice dosed with the PEG/PVP emulsion than in mice dosed with the DMA/lactate preparation, despite the 2-fold larger dose given to the latter group. Also, $N^4$-(3-bromo-phenyl)-$N^6$-methyl-pyrido[3,4-d]pyrimidine-4,6-diamine blood levels were 10-fold greater in the PEG/PVP group. None of the mice given the PEG/PVP preparation died, while all 3 mice dosed with the DMA/lactate system died. Thus, drug formulated as an emulsion in the PEG/PVP gave several advantages over a DMA/lactate system in which drug was suspended.

Example 2

Formulation

Butyl-[2,5-dimethyl-7-(2,4,6-trimethyl-phenyl)-7H-pyrrolo[2,3-d]pyrimidin-4-yl]-ethyl-amine (CRF-1 receptor antagonist) was formulated in the PEG/PVP system as follows. Thirty milligrams of Butyl-[2,5-dimethyl-7-(2,4,6-trimethyl-phenyl)-7H-pyrrolo[2,3-d]pyrimidin-4-yl]-ethyl-amine were dissolved in 1.5 g of molten (65° C.) PEG 3350. To the melted phase were then added 1.5 mL of 10% PVP in pH 7.4 phosphate buffer with stirring. The mixture was stirred during cool-down to room temperature. Before administration, the formulation was filtered through a 0.45 μm PTFE filter. Mean particle size was shown to be approximately 420 nm diameter. The final concentration was calculated to be 10 mg/mL.

Administration and Study Design

Single, 10-mg/kg oral gavage doses of the Butyl-[2,5-dimethyl-7-(2,4,6-trimethyl-phenyl)-7H-pyrrolo[2,3-d]pyrimidin-4-yl]-ethyl-amine PEG/PVP formulation were given to 3 fasted male Wistar rats. In parallel, single, 10-mg/kg oral gavage doses of Butyl-[2,5-dimethyl-7-(2,4,6-trimethyl-phenyl)-7H-pyrrolo[2,3-d]pyrimidin-4-yl]-ethyl-amine, as an aqueous suspension in 0.1% Tween 80, were administered to 3 additional fasted male Wistar rats. Blood samples were serially drawn over the 24-hour period following administration and assayed for Butyl-[2,5-dimethyl-7-(2,4,6-trimethyl-phenyl)-7H-pyrrolo[2,3-d]pyrimidin-4-yl]-ethyl-amine concentrations.

Results

Mean Butyl-[2,5-dimethyl-7-(2,4,6-trimethyl-phenyl)-7H-pyrrolo[2,3-d]pyrimidin-4-yl]-ethyl-amine Cmax for the PEG/PVP emulsion group was slightly higher than the 0.1% Tween group (283 ng/mL vs 267 ng/mL). AUC(0–8) was 283 ng•hr/mL for PEG/PVP-dosed rats, compared to 267 ng•hr/mL for the suspension-dosed mice. Neither Cmax, AUC(0–8), nor half-life differed significantly between the 2 dose groups. In this case, formulation of the compound as an emulsion in PEG/PVP offered no clear advantage over drug given as a simple suspension.

What is claimed is:

1. A liquid composition for the delivery of a pharmaceutical agent to a patient, the composition comprising:
   a. polyethylene glycol having a weight-average molecular weight in the range of about 1,300 to about 9,000;
   b. an aqueous solution containing from about 5% (w/v) to about 20% (w/v) polyvinylpyrrolidone with respect to the entire solution, the polyvinylpyrrolidone having a weight-average molecular weight in the range of about 2,000 to about 30,000;
   c. a biologically compatible buffer having a pH of about 1.0 to about 7.4; and
   d. a pharmaceutical agent selected from $N^4$-(3-Bromo-phenyl)-$N^6$-methyl-pyrido[3,4-d]pyrimidine-4,6-diamine or Butyl-[2,5-dimethyl-7-(2,4,6-trimethyl-phenyl-7H-pyrrolo[2,3-d]pyrimidin-4-yl]-ethyl-amine.

2. A composition in accordance with claim 1 wherein the polyethylene glycol has a weight-average molecular weight in the range of about 1,300 to about 4,800.

3. A composition in accordance with claim 1 wherein the polyethylene glycol has a weight-average molecular weight in the range of about 3,000 to about 4,800.

4. A composition in accordance with claim 1 wherein the polyvinylpyrrolidone is about 20% (w/v) of the aqueous solution.

5. A composition in accordance with claim 1 wherein the polyvinylpyrrolidone has a weight-average molecular weight of about 10,000.

6. A composition in accordance with claim 1 wherein the buffer is a phosphate buffer.

7. A composition in accordance with claim 1 wherein the polyethylene glycol is present in the composition in an amount that is in the range of about 20% to about 70% by volume of the composition.

8. A composition in accordance with claim 1 wherein the polyethylene glycol is present in the composition in an amount that is in the range of about 40% to about 60% by volume of the composition.

9. A composition in accordance with claim 1 wherein the polyethylene glycol is present in the composition in an amount that is about 50% by volume of the composition.

10. A composition in accordance with claim 1 wherein the aqueous solution is present in the composition in an amount that is in the range of about 20% to about 70% by volume of the composition.

11. A composition in accordance with claim 1 wherein the aqueous solution is present in the composition in an amount that is in the range of about 40% to about 60% by volume of the composition.

12. A composition in accordance with claim 1 wherein the aqueous solution is present in the composition in an amount that is about 50% by volume of the composition.

* * * * *